US007848559B2

United States Patent
Defrise et al.

(10) Patent No.: US 7,848,559 B2
(45) Date of Patent: Dec. 7, 2010

(54) DISCRETE AXIAL RE-BINNING OF TIME-OF-FLIGHT POSITRON EMISSION TOMOGRAPHY DATA

(75) Inventors: Michel Defrise, Brussels (BE); Vladimir Panin, Knoxville, TN (US); Christian J. Michel, Lenoir City, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1100 days.

(21) Appl. No.: 11/804,265

(22) Filed: May 17, 2007

(65) Prior Publication Data
US 2008/0099686 A1    May 1, 2008

Related U.S. Application Data

(60) Provisional application No. 60/801,198, filed on May 17, 2006.

(51) Int. Cl.
G06K 9/00    (2006.01)
(52) U.S. Cl. .............................. 382/132; 382/280

(58) Field of Classification Search ................ 382/128, 382/131, 132, 280; 250/363.04, 363.03
See application file for complete search history.

(56) References Cited

U.S. PATENT DOCUMENTS 7,417,231 B2 *  8/2008  Defrise et al. .......... 250/363.04
2007/0036418 A1 *  2/2007  Pan et al. .................... 382/131

OTHER PUBLICATIONS

Michel Defrise; Exact and Approximate rebinning algorithms for 3-D PET data; IEEE transactions on medical imaging, vol. 16, No. 2, Apr. 1997.*

* cited by examiner

*Primary Examiner*—Anand Bhatnagar
*Assistant Examiner*—Claire Wang
(74) *Attorney, Agent, or Firm*—Peter L. Kendall

(57) ABSTRACT

Axial rebinning methods are provided for 3D time-of-flight (TOF) positron emission tomography (PET), based on 2D data rebinning. Rebinning is performed separately for each axial plane parallel to the axis of the PET scanner. An analytical approach is provided that is based on a consistency condition for TOF-PET data with a gaussian profile. A fully discrete approach is also provided, wherein each 2D TOF-PET data is calculated as a linear combination of 3D TOF-PET data having the same sinogram coordinates s and ϕ.

11 Claims, 2 Drawing Sheets

DISCRETE AXIAL RE-BINNING OF TIME-OF-FLIGHT POSITRON EMISSION TOMOGRAPHY DATA

CLAIM OF PRIORITY FROM RELATED APPLICATION

This application claims priority under 35 U.S.C. §119(e) from copending Provisional Application Ser. No. 60/801,198, filed May 17, 2006.

FIELD OF THE INVENTION

The present invention generally relates to nuclear medicine, and systems for obtaining nuclear medicine images. In particular, the present invention relates to systems and methods for reconstructing nuclear medicine images from time-of-flight (TOF) positron emission tomography (PET) data.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred. An example of a PET method and apparatus is described in U.S. Pat. No. 6,858,847, which patent is incorporated herein by reference in its entirety.

After being sorted into parallel projections, the LORs defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LORs, where each set is parallel to a particular detector angle, and therefore represents a two dimensional parallel projection $p(s, \phi)$ of the three dimensional radionuclide distribution within the patient, where s corresponds to the distance along the imaging plane perpendicular to the scanner axis and $\phi$ corresponds to the angle of the detector plane with respect to the x axis in (x, y) coordinate space (in other words, ($\phi$ corresponds to a particular LOR direction). Coincidence events are integrated or collected for each LOR and stored as a sinogram. In this format, a single fixed point in f(x,y) traces a sinusoid in the sinogram. In each sinogram, there is one row containing the LORs for a particular azimuthal angle $\phi$; each such row corresponds to a one-dimensional parallel projection of the tracer distribution at a different coordinate along the scanner axis. This is shown conceptually in FIG. 1.

An event is registered if both crystals detect an annihilation photon within a coincidence time window $\tau$ (e.g., on the order of 4-5 ns), depending on the timing properties of the scintillator and the field of view. A pair of detectors is sensitive only to coincidence events occurring in the volume between the two detectors, thereby eliminating the need for physical collimation, and thus significantly increasing sensitivity. Accurate corrections can be made for the self-absorption of photons within the patient (i.e., attenuation correction) so that accurate measurements of tracer concentration can be made.

The number of time coincidences detected per second within a field of view (FOV) of a detector is the count rate of the detector. The count rate at each of two oppositely disposed detectors, A and B, can be referred to as singles counts, or singles, $S_A$ and $S_B$. The time required for a gamma photon to travel from its point of origin to a point of detection is referred to as the time of flight, or TOF, of the gamma photon. TOF is dependent upon the speed of light c and the distance traveled. A time coincidence, or coincidence event, is identified if the time difference between the arrival of signals in a pair of oppositely disposed detectors is less than a coincidence time window $\tau$.

As illustrated in FIG. 2, if an annihilation event occurs at the midpoint of a LOR, the TOF of the gamma photon detected in detector A ($T_A$) is equal to the TOF of the gamma photon detected in detector B ($T_B$). If an annihilation event occurs at a distance $\Delta x$ from the midpoint of the LOR, the difference between $T_A$ and $T_B$ is $\Delta t=2\Delta x/c$, where c is the speed of light. If d is the distance between the detectors, the TOF difference $\Delta t$ could take any value from $-d/c$ to $+d/c$, depending on the location of the annihilation event.

Time-of-flight (TOF) positron emission tomography (PET) ("TOF-PET") is based on the measurement of the difference $\Delta t$ between the detection times of the two gamma photons arising from the positron annihilation event. This measurement allows the annihilation event to be localized along the LOR with a resolution of about 75-120 mm FWHM, assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects.

TOF scanners developed in the early 1980s were used for research and clinical applications, but the SNR gain provided by the TOF measurements of about 500 ps resolution was offset by the low stopping power of the $BaF_2$ and CsF scintillation crystals used in such scanners. Image reconstruction for complete 2D TOF-PET data has been disclosed in the prior art. Early TOF scanners used a back project-then-filter (BPF) algorithm. The maximum-likelihood estimation algorithm (MLEM) also was adapted for list-mode TOF data, and shown to provide improved image quality compared to BPF.

The increased computation required to process the TOF data also led to the proposal of a faster iterative algorithm that was directly applied to the back-projected TOF data.

In contrast with 2D TOF reconstruction, few studies have been devoted to the 3D case, probably because the rise of 3D PET in the late 1980s overshadowed the interest for TOF. The Colsher filter and the 3D re-projection algorithm for axially truncated data generalized the 3D back projection filtered methods to TOF data.

However, the spatial resolution and sensitivity offered by those TOF systems could not compete with the values achieved with BGO scanners. As a result, TOF-PET almost completely disappeared from the scene in the 1990s. Today, faster electronics and crystals such as LSO and LaBr$_3$ reopen the prospect of exploiting the TOF information without compromising other parameters such as the count rate, the sensitivity, and the energy and spatial resolutions. This prospect motivates the present invention of fast reconstruction strategies for 3D TOF-PET.

However, while extending MLEM or MAP (Maximum A posteriori Probability) algorithms to 3D TOF-PET is conceptually straightforward, the computational load is an issue, because the number of data bins is now equal to the number of LORs (which exceeds $10^8$ in 3D PET even after axial undersampling using the 'span' concept) multiplied by the number of sampled TOF bins. What is needed is a feasible approach for reconstruction of 3D TOF-PET data.

SUMMARY OF THE INVENTION

The present invention solves the existing need in the art by providing a hybrid reconstruction method that re-bins the data onto a lower dimensional space and then applies a conventional 2D reconstruction. This approach requires access to either pre-corrected data or correction factors (e.g., sensitivity, random coincidences, attenuation and scatter). The hybrid method offers a good compromise between image quality and computational efficiency. The invention further makes the hypothesis that hybrid methods will also be effective for whole-body clinical TOF-PET imaging.

The first component of the hybrid approach according to the invention is the re-binning algorithm. Starting from pre-corrected TOF projection data acquired by a volume (i.e., 3D) PET scanner, a re-binning algorithm estimates for each transaxial slice the ordinary 2D data set. The re-binning algorithms according to the invention apply this procedure separately for each axial plane parallel to the axis of the scanner, and therefore are referred to as axial rebinning methods. An axial rebinning method thus does not mix LORs with different values of the ordinary sinogram variables s and $\phi$. In contrast, Fourier rebinning ("TOF-FORE") is not an axial method because the 2D Fourier transform introduces correlations between different transaxial s, $\phi$ samples.

There are several benefits to the axial approach. First, no arc correction is needed, such that the rebinned data can be obtained for the "native" transaxial arrangement of the detectors in the ring. Additionally, because each 3D TOF-LOR contributes to a smaller number of 2D TOF-LOR than with TOF-FORE, the axial approach may make online rebinning feasible.

The present invention provides two axial rebinning methods. The first method is based on a consistency condition for the 3D TOF data; it is an exact method in the limit of fine sampling and its derivation is similar to the derivation of FOREJ. The second method is discrete in the sense that it directly takes into account data sampling; the rebinning coefficients are pre-calculated by optimizing some cost function.

BRIEF DESCRIPTION OF THE DRAWINGS

The invention will now be more fully described by way of example with reference to the accompanying drawings in which.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Figure 1:
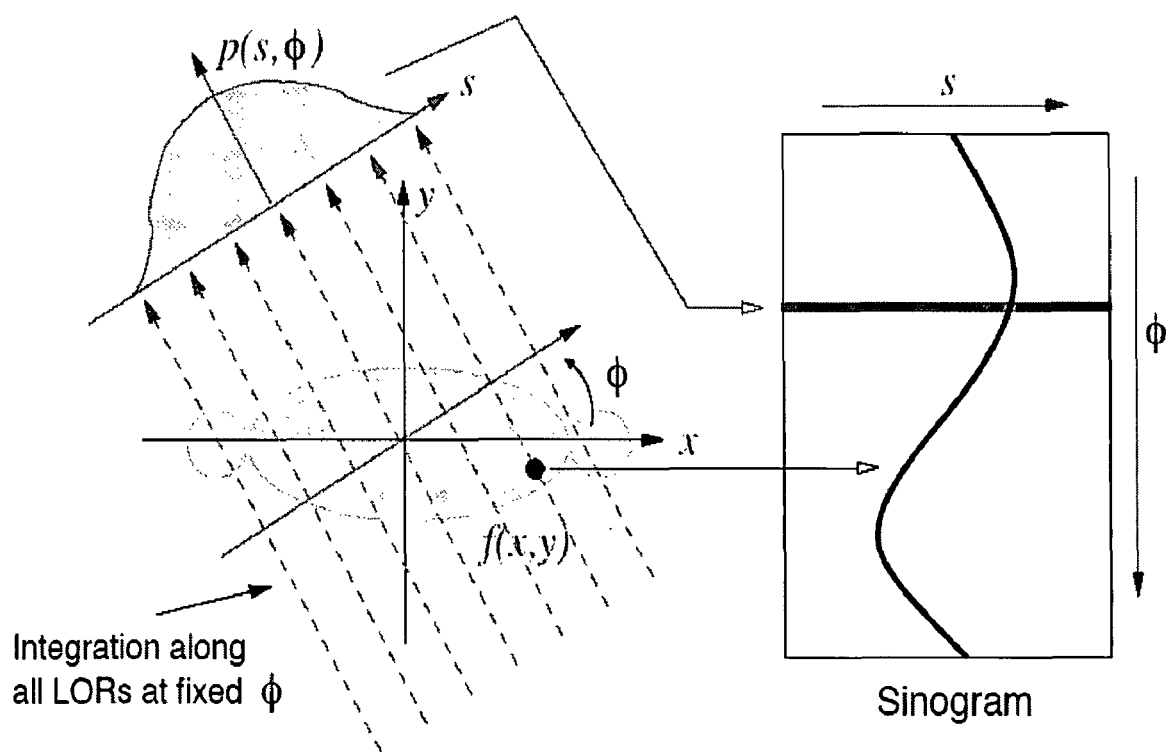
FIG. 1 is a diagram illustrating the relationship between PET projection data and a sinogram.
Figure 2:
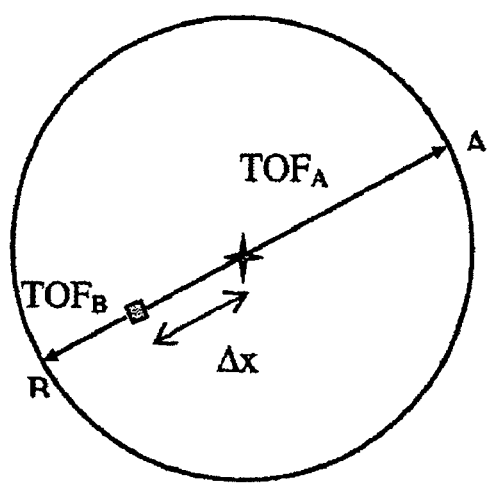
FIG. 2 is a diagram illustrating the concept of time of flight in PET imaging.
Figure 3:
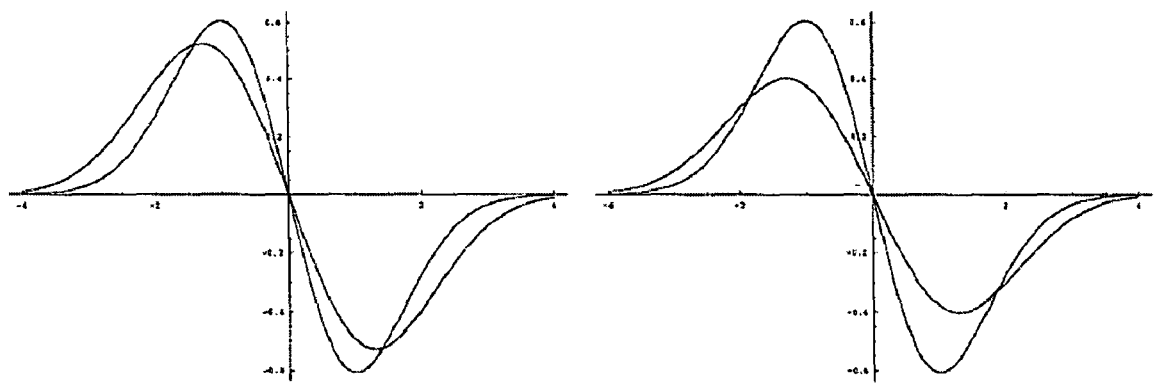
FIG. 3 illustrates exact and discrete integration profiles for a first time derivative in accordance with the present invention.

Initially, the measured TOF data is parameterized as $$p(t, s, \phi, z, \delta) = \sqrt{1+\delta^2} \int_{-\infty}^{\infty} dl f(s\cos\phi - l\sin\phi, s\sin\phi + l\cos\phi, z + l\delta) h(t - l\sqrt{1+\delta^2}) \quad (1)$$

where s and $\phi$ are the usual transaxial sinogram coordinates, z is the axial coordinate of the mid-point of the LOR and $\delta = \tan\theta$ is the tangent of the angle $\theta$ between the LOR and a transaxial plane. These parameters are illustrated in FIG. 3. The range of these variables is the same as for a non-TOF scanner.

For instance, for a cylindrical scanner with radius $R_d$, scanner axial length L and axial field of view $z \in [0,L]$, the range is $|s| \leq R_{FOV}$, $\phi \in [0, \pi)$, and $$|\delta|\sqrt{R_d^2 - s^2} \leq z \leq L - |\delta|\sqrt{R_d^2 - s^2} - \frac{L}{2\sqrt{R_d^2 - s^2}} \leq \delta \leq \frac{L}{2\sqrt{R_d^2 - s^2}} \quad (2)$$

where $R_{FOV}$ denotes the radius of the cylindrical support of $f$. Note that the integration variable l in equation (1) is the path length projected onto the transaxial plane, and is related to the path length r along the oblique LOR by $r = l\sqrt{1+\delta^2} = l/\cos\theta$.

In equation (1) the subscript t denotes the TOF bin, corresponding to a sensitivity profile h(t, r) centered at position r=t along the LOR. The TOF parameter is related to the difference $\Delta\tau$ between the arrival times of the two photons by $t = c\Delta\tau/2$, where c is the speed of light.

The aim of a re-binning algorithm is to estimate, for each time bin t, the 2D TOF sinogram of each transaxial slice z within the axial field-of-view of the scanner. This 2D TOF sinogram is defined by $$p_{reb}(t, s, \phi, z) = p(t, s, \phi, z, 0) \quad (3)$$

An efficient rebinning algorithm cannot be based only on equation (3) because it uses only the data subset that corresponds to δ=0 (or in practice, to |δ| smaller than some threshold). Instead, rebinning should incorporate the entire 3D data set to optimize the SNR.

Consider a Gaussian TOF profile $$h(t-l) = \exp(-(t-l)^2/2\sigma^2) \quad (4)$$

Where σ (the standard deviation of the TOF profile) is related to the full-width at half maximum $T_{FWHM}$ of the time difference measurement by $$\sigma = \frac{cT_{FWHM}}{4\sqrt{2\log 2}} \quad (5)$$

Then, any consistent data given by equation (1) for some arbitrary function $f(x,y,z)$ with a continuous derivative with respect to z must satisfy the following partial differential equation:

$$\frac{\partial p}{\partial \delta} - \frac{t}{\sqrt{1+\delta^2}} \frac{\partial p}{\partial z} + \frac{t\delta}{1+\delta^2} \frac{\partial p}{\partial t} = \frac{\sigma^2}{\sqrt{1+\delta^2}} \frac{\partial^2 p}{\partial z \partial t} - \frac{\delta \sigma^2}{1+\delta^2} \frac{\partial^2 p}{\partial t^2} \quad (6)$$

Exact Axial TOF Rebinning

For any $z_0$, $t_0$ the left-hand side of equation (6) can be written as a directional derivative in the z,δ,t space at fixed s, φ. For each fixed pair $z_0$, $t_0$ $$\frac{d}{d\delta} p\left(t_0\sqrt{1+\delta^2}, s, \phi, z_0 - t_0\delta, \delta\right) = \frac{\sigma^2}{\sqrt{1+\delta^2}} \frac{\partial^2 p}{\partial z \partial t} - \frac{\delta \sigma^2}{1+\delta^2} \frac{\partial^2 p}{\partial t^2} \quad (7)$$

where the omitted arguments of the derivatives of p in the right-hand side are the same as the arguments in the left-hand side of the equation (7). To confirm that the left-hand side of equations (6) and (7) coincide, note that $$\frac{d}{d\delta} t_0\sqrt{1+\delta^2} = \frac{\delta t_0}{\sqrt{1+\delta^2}} = \frac{\delta}{1+\delta^2}\left(t_0\sqrt{1+\delta^2}\right) \quad (8)$$

$$\frac{d}{d\delta}(z_0 - t_0\delta) = -t_0 = \frac{-1}{\sqrt{1+\delta^2}}\left(t_0\sqrt{1+\delta^2}\right)$$

For a fixed $z_0$, $t_0$, equation (7) is integrated with respect to δ between δ=0 and δ=$\delta_1$. This yields $$p(t_0, s, \phi, z_0, 0) = p\left(t_0\sqrt{1+\delta_1^2}, s, \phi, z_0 - t_0\delta_1, \delta_1\right) - \quad (9)$$

$$\sigma^2 \int_0^{\delta_1} d\delta \left(\frac{1}{\sqrt{1+\delta^2}} \frac{\partial^2 p}{\partial z \partial t} - \frac{\delta}{1+\delta^2} \frac{\partial^2 p}{\partial t^2}\right)$$

$$\left(t_0\sqrt{1+\delta^2}, s, \phi, z_0 - t_0\delta, \delta\right)$$

Equation (9) provides an independent estimate of the rebinned data for each obliquity $\delta_1$, such that the data are known in a neighborhood of $t=t_0\sqrt{1+\partial_1^2}$, $z=z_0-t_0\partial_1, \partial_1$. Taking the average over the range $\partial_1 \epsilon [\partial_a(z_0,t_0)\partial_b(z_0,t_0)]$, and commuting the integrals over ∂ and $\partial_1$, the following exact rebinning algorithm is obtained:

$$p_{reb}(t_0, s, \phi, z_0) = \quad (10)$$

$$\frac{1}{\delta_b(z_0, t_0) - \delta_a(z_0, t_0)} \int_{\delta_a}^{\delta_b} d\delta \left\{ p\left(t_0\sqrt{1+\delta^2}, s, \phi, z_0 - t_0\delta, \delta\right) - \right.$$

$$\sigma^2 w(\delta_a, \delta_b, \delta)\left(\frac{1}{\sqrt{1+\delta^2}} \frac{\partial^2 p}{\partial z \partial t} - \frac{\delta}{1+\delta^2} \frac{\partial^2 p}{\partial t^2}\right)$$

$$\left.\left(t_0\sqrt{1+\delta^2}, s, \phi, z_0 - t_0\delta, \delta\right)\right\}$$

with the discontinuous integration profile $$w(\delta_a, \delta_b, \delta) = \begin{cases} \delta_b - \delta & \delta > 0 \\ \delta_a - \delta & \delta < 0 \end{cases} \quad (11)$$

Here, the obliquity range is given by $$\delta_b(z_0, t_0) = \min\left\{\frac{L-z_0}{R_d - t_0}, \frac{z_0}{R_d + t_0}, \delta_{max}\right\} \quad (12)$$

$$\delta_a(z_0, t_0) = \max\left\{\frac{-L+z_0}{R_d + t_0}, \frac{-z_0}{R_d - t_0}, -\delta_{max}\right\}$$

where $\partial_{max} \leq L/2R_d$ is the maximum value of δ included in the reconstruction, L is the axial length of the scanner, and $R_d$ is its radius. The rebinning equation (10) is axial in that it does not mix different s,φ. This has several advantages over Fourier rebinning as discussed above. Additionally, because a given bin t, s, φ, z, d contributes only to a small number of LORs, on-line list mode rebinning may be possible.

When the TOF data are binned with a uniform sampling interval Δt, the effective h(t) profile is the convolution of the TOF gaussian with a door function of width Δt. Numerically, the resulting profile can be approximated to a high accuracy by a gaussian profile of slightly larger standard deviation $\sigma_{effective}$ that is well-fitted empirically by $$\sigma_{effective} \simeq \sigma\left(1 + 0.04\left(\frac{\Delta t}{\sigma}\right)^2\right) \quad (13)$$

The calculation of the second derivatives with respect to t and z amplifies noise. The correction term can be smoothed in the variables s, φ to minimize this problem, taking into account the fact that the correction is small and that TOF data tolerate a poorer angular (φ) sampling than non-TOF data.

Despite the fact that the sampling interval Δt in t is fairly large in practice (on the order of σ), the t derivatives can be calculated with good accuracy because the TOF data p is an essentially band-limited function in the variable t. A good approximation can be obtained as $$\frac{\partial p}{\partial t} \simeq \frac{\xi}{2\Delta t}(p(t+\Delta t, \ldots) - p(t-\Delta t, \ldots)) \quad (14)$$

where the parameter ξ is determined empirically in such a way that for all x, $$\frac{\xi}{2\Delta t}\left(e^{-(x-\Delta t)^2/(2\sigma^2)} - e^{-(x+\Delta t)^2/(2\sigma^2)}\right) \simeq \frac{x}{\sigma^2}e^{-x^2/(2\sigma^2)} \quad (15)$$

Similarly, for the second derivative a good approximation is $$\frac{\partial^2 p}{\partial t^2} \simeq \frac{\eta}{\Delta t^2}(p(t+\Delta t, \ldots) + p(t-\Delta t, \ldots) - 2p(t, \ldots)) \quad (16)$$

provided $\eta$ is such that $$\frac{\eta}{\Delta t^2}\left(e^{-(x-\Delta t)^2/(2\sigma^2)} + e^{-(x+\Delta t)^2/(2\sigma^2)} - 2e^{-x^2/(2\sigma^2)}\right) \simeq \frac{d^2}{dx^2}e^{-x^2/(2\sigma^2)} \quad (17)$$

The values of the parameters $\xi$ and $\eta$ that minimize the squared error for equations (15) and (17) over x are given in Table 1 below for a few typical values of the sampling ratio $\Delta t/\sigma$. At the limit of fine sampling $\Delta t \to 0$, these parameters tend to the usual value of 1.

TABLE 1

| | FWHM | | | | | | | |
|---|---|---|---|---|---|---|---|---|
| $\Delta t$ | 0.1 | 0.2 | 0.3 | 0.4 | 0.5 | 0.6 | 0.7 | 0.8 |
| $\xi$ | 1.01 | 1.05 | 1.12 | 1.21 | 1.31 | 1.40 | 1.47 | 1.50 |
| $\eta$ | 1.01 | 1.05 | 1.10 | 1.18 | 1.29 | 1.41 | 1.55 | 1.69 |

Discrete Axial TOF Rebinning

The second approach to axial rebinning is discrete in the sense that each 2D TOF-LOR is calculated as a linear combination of the 3D TOF-LOR with the same (s,φ). The coefficients of the linear combination are pre-computed by optimizing a cost function that enforces both accuracy and good variance reduction. The cost function models the TOF profile, the axial PSF (point spread function) of the LORs, and the specific axial sampling pattern of the data.

After discretization of the exact rebinning equation (10), each rebinned 2D TOF-LOR is calculated as a weighted average of the 3D TOF-LORs in the same axial plane (i.e., with the same s,φ). The coefficients of this weighted average will be referred to as the rebinning coefficients. Instead of deriving these coefficients by discretization of the continuous rebinning formula, in accordance with this embodiment of the invention the rebinning coefficients are estimated by minimizing a cost function that models the data sampling and the axial width of the detectors. This cost function accounts for both the bias and the variance. With this approach the rebinning coefficients can be calculated off-line and stored in a lookup table.

In the discrete approach the axial profile of each tube of response (TOR) is modeled as a function w(z). As the rebinning is a for a fixed axial plane, the variables s, φ are omitted from all equations. Let a uniform and linear profile be $$w(x) = \begin{cases} 1 - 2|x|/\Delta & |z| \leq \Delta/2 \\ 0 & |z| > \Delta/2 \end{cases} \quad (18)$$

where $\Delta$ is the axial spacing between adjacent detector rings. After convolving the 3D TOF data with the profile w, the measured data are modeled as $$p_w(t, z, \delta) = \int dz' w(z-z')\sqrt{1+\delta^2} \int_{-\infty}^{\infty} dl f(l, z'+l\delta) \quad (19)$$

$$h\left(t - l\sqrt{1+\delta^2}\right)$$

$$= \int dz' \int dl f(l, z') k_w(t, z, \delta; l, z')$$

where $$k_w(t, z, \delta; l, z') = \sqrt{1+\delta^2}\, h\left(t - l\sqrt{1+\delta^2}\right) w(z-z'+l\delta) \quad (20)$$

is the 2D sensitivity profile of the TOR in the axial plane (s,φ). In practice $p_w$ is measured for a set of discrete samples $(t_j, z_j, \delta_j)$, $j=1, \ldots, N$. The derivation below can be applied to any sampling scheme, with or without axial spanning.

The aim is to estimate, with the smallest possible variance and bias, the 2D TOF-LOR $p_{reb}(t_k, z_k)$ for a set of samples $(t_k, z_k)$, $k=1, \ldots, N_{reb}$, where $z_k$ denotes the axial coordinates of the transaxial sections to be reconstructed, and $t_k$ are the chosen time bin samples for the rebinned data. The most general linear axial rebinning is then given as $$p_{reb}(t_k, z_k) \simeq \sum_{j=1}^{N} A_{k,j} p_w(t_j, z_j, \delta_j) \quad k = 1, \ldots, N_{reb}. \quad (21)$$

where the rebinning coefficients $A_{k,j}$ are designed to satisfy two constraints: First, in order for equation (21) to hold to a good accuracy for any function $f$; it is required that for each $l,z'$ within the field of view, $$k_w(t_k, z_k, 0; l, z') \simeq \sum_{j=1}^{N} A_{k,j} k_w(t_j, z_j, \delta_j; l, z') \quad (22)$$

Second, if the variance of the 3D LOR samples is locally uniform, the variance of the rebinned data $p_{reb}(t_k, z_k)$ in equation (21) will be proportional to the quantity $$\sum_{j=1}^{N} A_{k,j}^2 \quad (23)$$

and therefore this quantity should be kept as small as possible.

To satisfy these constraints a hyperparameter $\lambda$ is introduced, and the rebinning coefficients $A_{k,j}$ are determined that minimize the function $$\mathcal{L}_k = \int dz' \int dl \left\{ \frac{\sum_{j=1}^{N} A_{k,j} k_w(t_j, z_j, \delta_j; l, z') -}{k_w(t_k, z_k, 0; l, z')} \right\}^2 + \lambda \sum_{j=1}^{N} A_{k,j}^2 \quad (24)$$

This minimization must be done separately for each rebinned sample $k=1, \ldots, N_{reb}$. By solving the equations $\partial \mathcal{L}_k / \partial A_{k,j} = 0$ one obtains the optimal rebinning coefficients $$A_{k,j} = \sum_{j'=1}^{N} M_{j,j'}^{-1} V_{k,j'} \quad j = 1, \ldots, N \quad (25)$$

with the N-dimensional vector $$V_{k,j} = \int dz' \int dl \, k_w(t_j, z_j, \delta_j; l, z') k_w(t_k, z_k, 0; l, z') \quad (26)$$

where $M^{-1}$ is the inverse of the N×N Gramm matrix $$M_{j,j'} = \lambda \delta_{j,j'} + \int dz' \int dl \, k_w(t_j, z_j, \delta_j; l, z') k_w(t_{j'}, z_{j'}, \delta_{j'}; l, z')$$
$$j, j' = 1, \ldots, N \quad (27)$$

where $\partial_{j,j'}$ is the Kronecker symbol (not to be confused with obliquity variable).

Finally it is noted that the discrete rebinning approach can be generalized, for instance, by incorporating in the definition of the cost function an integration weight $\rho(z'-z_k) \cong (z'-z_k)^2$ that would give more weight to error contribution arising at larger axial distance from the desired rebinned LOR k.

Inserting the sensitivity profile (equation (20)) and the triangular axial profile (equation (18)) into equation (27) yields the simpler expression $$M_{j,j'} = \lambda \delta_{j,j'} + \int_{-R_d}^{R_d} dl \sqrt{1+\delta_j^2} \, h\left(t_j - l\sqrt{1+\delta_j^2}\right) \times \times \quad (28)$$
$$\sqrt{1+\delta_{j'}^2} \, h\left(t_{j'} - l\sqrt{1+\delta_{j'}^2}\right) b_w(z_j - z_{j'} + l\delta_j - l\delta_{j'})$$

where the integral should be limited if possible to the known diameter of the patient, and where $$b_w(z) = \int dz' w(z') w(z+z') \quad (29)$$

is the cubic spline $$b_w(z) = \begin{cases} \Delta\left(\frac{1}{3} - 2\frac{|z|^2}{\Delta^2} + 2\frac{|z|^3}{\Delta^3}\right) & |z| \le \Delta/2 \\ \Delta\left(\frac{2}{3} - 2\frac{|z|}{\Delta} + 2\frac{|z|^2}{\Delta^2} - \frac{2}{3}\frac{|z|^3}{\Delta^3}\right) & \Delta/2 < |z| \le \Delta \\ 0 & \Delta < |z| \end{cases} \quad (30)$$

Using equation (28) the elements of the Gramm matrix M are easily calculated with a one dimensional quadrature formula. If needed a more accurate model of the axial LOR profile w(z) can be used (where only the function $b_w$ needs to be modified). Following the same steps the vector V in equation (26) becomes $$V_{k,j} = \int_{-R_d}^{R_d} dl \sqrt{1+\delta_j^2} \, h\left(t_j - l\sqrt{1+\delta_j^2}\right) h(t_k - l) b_w(z_j - z_k + l\delta_j) \quad (31)$$

The hyperparameter $\lambda$ determines the compromise between bias and variance. Thus, if $\lambda=0$, the bias is minimized. It is consequently desirable to define a normalized hyperparameter $$\tilde{\lambda} = \frac{\lambda}{\|M\|^2} \quad (32)$$

and to select $\tilde{\lambda}$ between 0 and 1.

The pre-calculation of the rebinning coefficients can be simplified if rotational invariance with respect to $\phi$ is assumed. Further, the radial sinogram variable s induces only a small variation of order $O(s^2/R^2)$ of the sampled values of $\partial_j$, $$\delta = \frac{z_{ring2} - z_{ring1}}{2\sqrt{R_d^2 - s^2}} = \frac{z_{ring2} - z_{ring1}}{2R_d} + O(s^2/R_d^2) \quad (34)$$

If this small variation is neglected, the matrix M is then independent of s and $\phi$, and one needs only to perform a single matrix inversion. If a rebinned sample $(t_k, z_k)$ is required to depend only on a small subset of neighboring 3D samples, then the matrix M is smaller than N×N. With this approach one needs to pre-determine for each rebinning TOF-LOR k the subset of 3D TOF-LORs that makes a significant contribution. In this case $N_{reb}$ smaller matrices must be inverted.

If the hyperparameter $\lambda$ is large, normalization of the rebinning coefficients may be problematic because of the second term in the cost function equation (24). Consequently, a third normalization constraint may be added:

$$\sum_{j=1}^{N} A_{k,j} \sqrt{1+\delta_j^2} = 1 \quad k = 1, \ldots, N_{reb} \quad (35)$$

that guarantees exact rebinning for any object function such that $\partial f/\partial z = 0$. Introducing a Lagrange multiplier $w_k$ and minimizing $L_k$ under the constraint (35), we obtain the normalized rebinning coefficients $$A_{k,j} = \sum_{j'=1}^{N} M_{j,j'}^{-1} \left(V_{k,j'} + \omega_k \sqrt{1+\delta_{j'}^2}\right) \quad j = 1, \ldots, N \quad (36)$$

where $$\omega_k = \left(1 - \sum_{j'=1}^{N} \sum_{j=1}^{N} \sqrt{1+\delta_j^2} \, M_{j,j'}^{-1} V_{k,j'}\right) \bigg/ \left(\sum_{j'=1}^{N} \sum_{j=1}^{N} \sqrt{1+\delta_j^2} \, M_{j,j'}^{-1} \sqrt{1+\delta_{j'}^2}\right) \quad (37)$$

Figure 4:
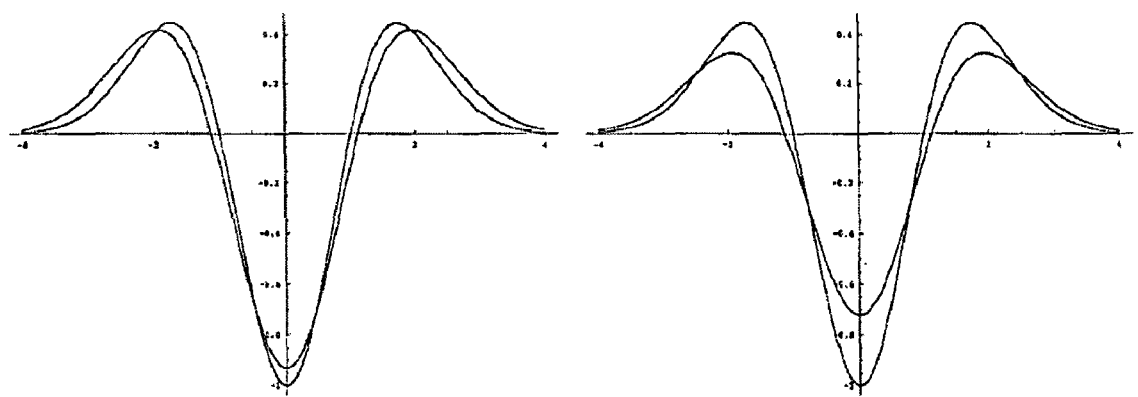
FIG. 4 illustrates exact and discrete integration profiles for a second time derivative in accordance with the present invention.

FIG. 3 illustrates discrete (left-hand side) and exact (right-hand side) integration profiles for the first time derivative with $\Delta t=0.5$ FWHM. FIG. 4 illustrates discrete (left-hand side) and exact (right-hand side) integration profiles for the second time derivative with $\Delta t=0.5$ FWHM.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method for reconstructing a nuclear medical image from TOF-PET imaging data, comprising the steps of:
obtaining three dimensional TOF-PET data from a PET scanner represented by the following equation:

$$p(t, s, \phi, z, \delta) = \sqrt{1+\delta^2} \int_{-\infty}^{\infty} dl f(s\cos\phi - l\sin\phi, s\sin\phi + l\cos\phi, z + l\delta) h(t - l\sqrt{1+\delta^2});$$

storing said TOF-PET data in a plurality of TOF time bins, each bin corresponding to a time difference value of photons arriving at opposite detectors of said PET scanner;
estimating, for each time bin and separately for each axial plane $(s,\phi)$ a two dimensional TOF sinogram of each transaxial slice z within an axial field of view of said scanner, based on the following relation:

$$p(t_0, s, \phi, z_0, 0) = p\left(t_0\sqrt{1+\delta_1^2}, s, \phi, z_0 - t_0\delta_1, \delta_1\right) - \sigma_2 \int_0^{\delta_1} d\delta \left(\frac{1}{\sqrt{1+\delta^2}} \frac{\partial^2 p}{\partial z \partial t} - \frac{\delta}{1+\delta^2} \frac{\partial^2 p}{\partial t^2}\right)(t_0\sqrt{1+\delta^2}, s, \phi, z_0 - t_0\delta, \delta);$$

and
reconstructing an image from said estimated two dimensional TOF sinograms using a two dimensional TOF reconstruction algorithm.

2. The method of claim 1, wherein the step of estimating comprises the step of modifying said three dimensional TOF-PET data to $$p_{reb}(t_0, s, \phi, z_0) = \frac{1}{\delta_b(z_0, t_0) - \delta_a(z_0, t_0)} \int_{\delta_a}^{\delta_b} d\delta \left\{ p\left(t_0\sqrt{1+\delta^2}, s, \phi, z_0 - t_0\delta, \delta\right) - \sigma^2 w(\delta_a, \delta_b, \delta) \left(\frac{1}{\sqrt{1+\delta^2}} \frac{\partial^2 p}{\partial z \partial t} - \frac{\delta}{1+\delta^2} \frac{\partial^2 p}{\partial t^2}\right) \left(t_0\sqrt{1+\delta^2}, s, \phi, z_0 - t_0\delta, \delta\right) \right\}.$$

3. The method of claim 2, wherein $$\delta_b(z_0, t_0) = \min\left\{\frac{L - z_0}{R_d - t_0}, \frac{z_0}{R_d + t_0}, \delta_{max}\right\}$$

$$\delta_a(z_0, t_0) = \max\left\{\frac{-L + z_0}{R_d + t_0}, \frac{-z_0}{R_d - t_0}, -\delta_{max}\right\}.$$

4. The method of claim 2, wherein the step of storing comprises using TOF time bins with a uniform sampling interval $\Delta t$, such that the TOF data has a profile corresponding to a convolution of a gaussian profile with a door function of width $\Delta t$, said profile having a standard deviation $\sigma_{effective}$ corresponding to $$\sigma_{effective} \simeq \sigma\left(1 + 0.04\left(\frac{\Delta t}{\sigma}\right)^2\right).$$

5. The method of claim 2, wherein said TOF data $w(\delta_a, \delta_b, \delta)$ is modeled as a discontinuous integration profile corresponding to $$w(\delta_a, \delta_b, \delta) = \begin{cases} \delta_b - \delta & \delta > 0 \\ \delta_a - \delta & \delta < 0 \end{cases}.$$

6. The method of claim 1, further comprising the step of convolving said three dimensional TOF-PET data with uniform linear profile w(x) corresponding to $$w(x) = \begin{cases} 1 - 2|x|/\Delta & |z| \leq \Delta/2 \\ 0 & |z| > \Delta/2 \end{cases}.$$

7. The method of claim 6, wherein said convolved three dimensional TOF-PET data are modeled as $$p_w(t, z, \delta) = \int dz' w(z - z')\sqrt{1+\delta^2} \int_{-\infty}^{\infty} dl f(l, z' + l\delta) h\left(t - l\sqrt{1+\delta^2}\right)$$
$$= \int dz' \int dl f(l, z') k_w(t, z, \delta; l, z').$$

8. The method of claim 7, further comprising the step of estimating comprises modifying said convolved three dimensional TOF-PET data to $$p_{reb}(t_k, z_k) \simeq \sum_{j=1}^{N} A_{k,j} p_w(t_j, z_j, \delta_j) \quad k = 1, \ldots, N_{reb}.$$

9. The method of claim 8, wherein for each l, z' within the field of view of said scanner, $$k_w(t_k, z_k, 0; l, z') \simeq \sum_{j=1}^{N} A_{k,j} k_w(t_j, z_j, \delta_j; l, z').$$

10. The method of claim 8, wherein if the variance of the three dimensional TOF-PET data is locally uniform, the variance of rebinned data is proportional to $$\sum_{j=1}^{N} A_{k,j}^2$$

and is kept as small as possible.

11. The method of claim 10, wherein the coefficients $A_{k,j}$ are determined so as to minimize the following equation:

$$\mathcal{L}_k = \int dz' \int dl \left\{ \sum_{j=1}^{N} A_{k,j} k_w(t_j, z_j, \delta_j; l, z') - k_w(t_k, z_k, 0; l, z') \right\}^2 + \lambda \sum_{j=1}^{N} A_{k,j}^2$$

where $\lambda$ is a hyperparameter having a preselected numerical value.

* * * * *